United States Patent [19]

Engelbrecht et al.

[11] 4,268,920
[45] May 26, 1981

[54] ENDOPROSTHESIS FOR A KNEE JOINT

[75] Inventors: Eckart Engelbrecht, Hamburg; Elmar Nieder, Jork, both of Fed. Rep. of Germany

[73] Assignee: GMT Gesellschaft für med. Technik mbH, Hamburg, Fed. Rep. of Germany

[21] Appl. No.: 946,872

[22] Filed: Sep. 29, 1978

[30] Foreign Application Priority Data

Oct. 5, 1977 [DE] Fed. Rep. of Germany ....... 2744710

[51] Int. Cl.³ ............................................... A61F 1/03
[52] U.S. Cl. .................................. 3/1.911; 128/92 C
[58] Field of Search ........................ 3/1.9, 1.91, 1.911, 3/1.912, 1.913; 128/92 C, 92 CA

[56] References Cited

U.S. PATENT DOCUMENTS

| 3,688,316 | 9/1972 | Lagrange et al. | 3/1.911 |
| 3,765,033 | 10/1973 | Goldberg et al. | 3/1.911 |
| 3,824,630 | 7/1974 | Johnston | 128/92 CX |
| 3,837,009 | 9/1974 | Walker | 3/1.911 |
| 3,868,730 | 3/1975 | Kaufer et al. | 3/1.91 |
| 3,918,101 | 11/1975 | Lagrange et al. | 3/1.911 |
| 4,001,896 | 1/1977 | Arkangel | 3/1.911 X |
| 4,115,875 | 9/1978 | Rambert et al. | 128/92 CA X |
| 4,167,047 | 9/1979 | Grundei et al. | 3/1.911 |

Primary Examiner—Clifford D. Crowder
Attorney, Agent, or Firm—Spencer & Kaye

[57] ABSTRACT

A knee joint endoprosthesis includes a femoral component, a tibial component and a slide bearing providing for relative pivotal movement between the components and formed of a femoral bearing half carried by the femoral component and a tibial bearing half carried by the tibial component. The bearing halves are arranged for being pressed to one another while free from being connected to one another. There is further provided an arrangement for cardanically guiding the bearing halves with respect to one another with degrees of freedom in horizontal and vertical directions.

32 Claims, 10 Drawing Figures

ENDOPROSTHESIS FOR A KNEE JOINT

BACKGROUND OF THE INVENTION

The invention relates to an endoprosthesis for a knee joint, including a femoral and a tibial component between which a slide bearing is disposed which comprises a femoral and a tibial bearing half.

The prior art endoprostheses have only one degree of freedom: they can be flexed or extended in only one plane.

Additionally, first models of rotary prostheses have become known which are capable of providing to a certain extent rotation of the lower leg with respect to the thigh as it is possible with a natural knee joint. However, such rotation is imparted undamped to the anchors with which the bearing halves are fastened to the bone. The rotary moment effecting the rotation is thus transmitted to the anchors by a hard jolt. Such impact stresses involve the danger of loosening the anchors to the bone.

The same danger is present if the knee joint prosthesis is bent to such a degree that parts of the tibial component abut on the femoral component. This also generates impact stresses which may loosen the anchors of the components in their associated bones.

SUMMARY OF THE INVENTION

It is therefore an object of the present invention to improve an endoprosthesis of the above-mentioned type in such a way that the transmission of impact stresses to the anchors of the prosthesis components is substantially avoided.

This object and others to become apparent as the specification progresses, are accomplished by the invention, according to which, briefly stated, the two bearing halves exert a compression stress on one another without being connected and are mutually cardanically guided with degrees of freedom in a vertical as well as horizontal direction.

The endoprosthesis according to the invention permits its wearer to use his knee joint in a substantially natural sequence of movements. The two bearing halves are movable with respect to one another over a natural range and the movements are attenuated by the soft tissues surrounding the knee joint. If the knee joint is flexed extensively, the two bearing halves are lifted away from one another against the resistance of the soft tissue, so that the joint swings resiliently and with attenuation into the range of greatest flexion. In a similar manner, the two bearing halves are lifted away from one another also upon the introduction of rotary moments in the lower leg or in the thigh, respectively; this occurrence also pretensions the soft tissue. This pretensioning attenuates the rotary movement; this attenuation prevents the introduction of impact stresses into the anchors.

Moreover, the prosthesis according to the invention has the advantage that the two bearing halves can each be inserted separately from the other into the femur or the tibia, respectively. The two bearing haves are joined only at the most favorable moment in the course of the operation.

According to a preferred embodiment of the invention, the slide bearing includes a part absorbing the compression stresses and a part absorbing the tensile stresses, each of which again has at least one femoral and one tibial bearing half. With this separation of function it is possible to design each one of the two parts optimally for its respective function with the elimination of any mutual interference in the performance of these functions. The part absorbing the compression stresses is provided with broad, mutually stressing faces which have the result that the occurring areal pressures are small. This arrangement is thus essentially a replica of the natural knee joint. The part absorbing the tensile stresses lies outside of the plane which transmits the compression stresses. It can thus be made large enough so that the areal pressures can be kept low. Moreover, this part is arranged to be movable with respect to the part transmitting the compression stresses, in the direction of the occurring compression or tensile stresses so that both parts can move independently of one another.

DESCRIPTION OF THE PREFERRED EMBODIMENTS

Figures 9, 10:
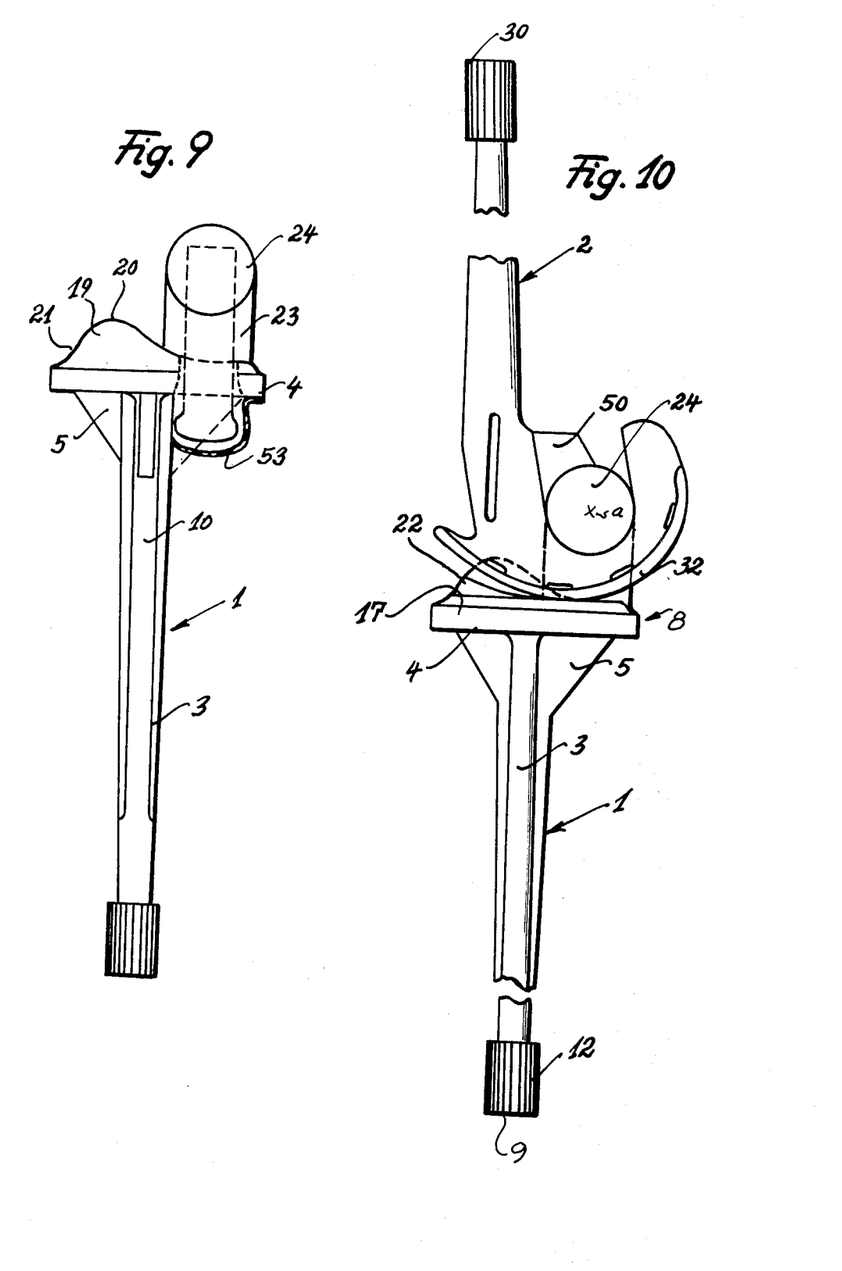
FIG. 9 is a partially sectional elevational view of another preferred embodiment of the tibial component.
FIG. 10 is a side elevational view of an assembled knee joint prosthesis according to the invention.

Turning first to FIG. 10, the endoprosthesis of a knee joint shown therein essentially includes a tibial component 1 and a femoral component 2. The tibial component 1 comprises a stem 3, having, at the top, an abutment or platform 4 which is additionally supported on the stem 3 by means of ribs 5. The stem 3 is connected with the abutment 4 approximately at the center of gravity of the latter. Also referring to FIG. 4, the upper side 6 of the abutment 4 facing away from the stem 3 is designed as a planar surface with edges which have a collar 7 protruding from the top side 6. The collar 7 serves as a mount for a tibial bearing half 8 of a bearing member which absorbs compression-stresses and which is arranged on the top side 6.

Figures 2, 4, 4A:
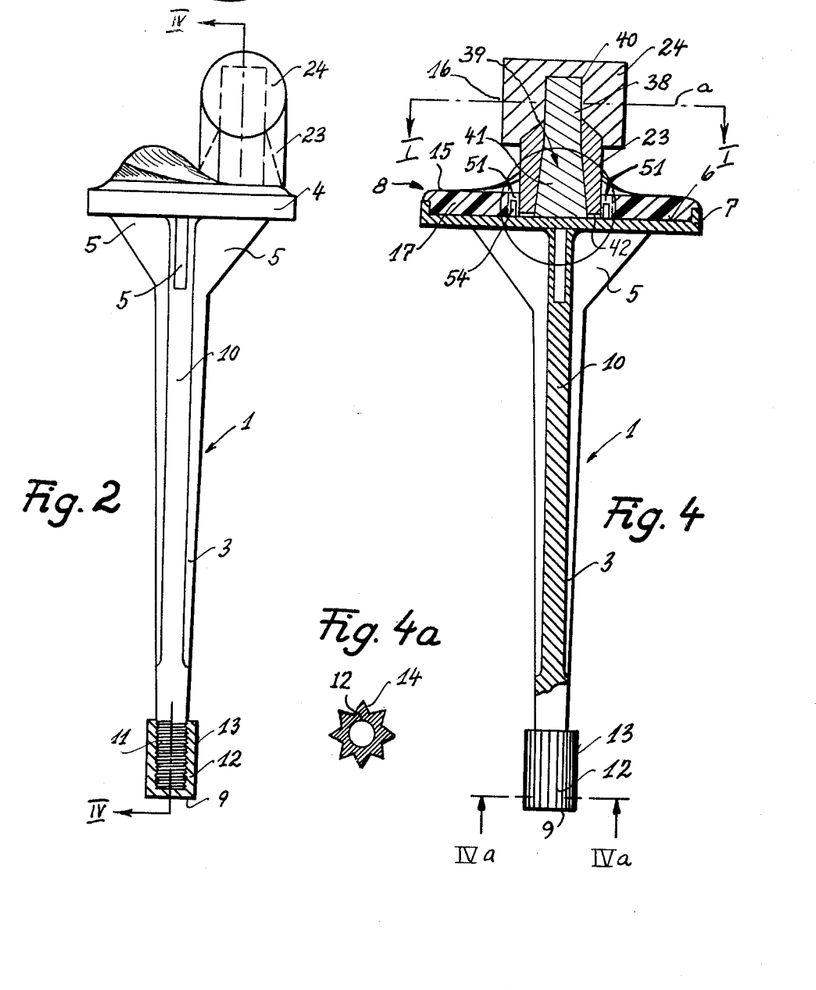
FIG. 2 is a partially sectional elevational view of the tibial component.
FIG. 4 is a longitudinal sectional view along the section line IV—IV of FIG. 2.
FIG. 4a is a sectional view taken along line IVa—IVa of FIG. 4.

The stem 3 is conically tapered in the direction from the abutment 4 toward its end 9 which is to be pushed into the bone. In order to stiffen the stem 3, ribs 10 are provided which extend preferably from all four, but at least from two sides of the stem 3. At the end 9, a thread 11 is provided on the stem 3, as shown in FIG. 2. A cap 12 is screwed onto this thread. The outer circumference 13 of the cap 12 serves as a guide for the stem 3 in the bone which receives the stem. As shown in FIG. 4a, the outer circumference 13 of the cap 12 is provided with grooves 14 which extend approximately parallel to the longitudinal direction of the stem 3. The connecting material, for example the bone cement, is squeezed through the grooves 14 from the end 9 in the direction toward the abutment 4 when the stem 3 is introduced into the bone cavity filled with bone cement.

Figure 1:
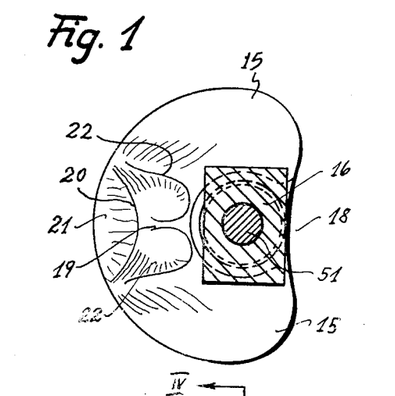
FIG. 1 is a sectional view, along line I—I of FIG. 4, of a preferred embodiment of the tibial component forming part of the endoprosthesis according to the invention.
Figure 3:
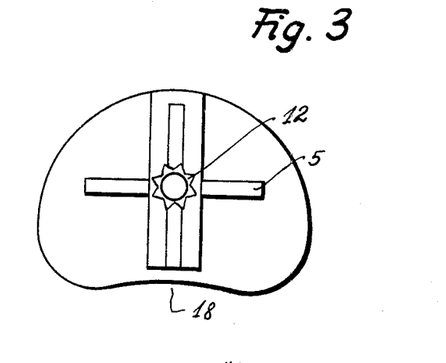
FIG. 3 is a bottom plan view of the tibial component.

The tibial bearing half 8 essentially includes a part in the form of planar surfaces 15 which absorb the compression stresses. The planar surfaces 15 are formed on an insert 17 which rests with a flat bottom face on the top side 6 of the abutment 4 and is secured against shifting by the collar 7. The planar surfaces 15 are formed at the edge regions of insert 17 disposed transversely to the plane of flexion. As seen in FIGS. 1 and 3, the edges of the insert 17 are approximately circular and have a recess 18 which is provided only in the region of a center part disposed between the two edge portions of the planar surfaces 15 and which is oriented toward the center part. In this way, the abutment 4 and its matching insert 17 are given the shape of a horseshoe on whose arms the planar surfaces 15 are formed.

In the center portion of the tibial component 1 disposed between the arms of insert 17, a Cardan bearing 16 rises from the rear of the center portion adjacent the recess 18. An elevation or abutment face 19 is provided ahead of the Cardan bearing 16 in the plane of flexion when seen in the direction toward the knee cap. This elevation 19 rises from the insert 17 and ends in a ridge 20 which extends in a curve from one planar surface 15 to the other.

On the other side of the ridge 20, the abutment face 19 continues in a steep slope 21 in the direction toward the collar 7 which surrounds the entire insert 17. The slope 21 as well as the abutment face 19 facing away from it extend essentially in the plane of flexion. To both sides, the elevation or abutment face 19 descends in the direction toward the arms of the planar surfaces 15 in the form of lateral faces 22 which open into the planar surface 15. The side faces 22 are curved in the direction toward the abutment face 19 in such a manner that a rolling movement of the femoral bearing half 2 in the direction of flexion cannot be interfered with.

The Cardan bearing 16 essentially includes a sleeve member 23 which rises from the insert 17 and whose axis is essentially perpendicular to the planar surfaces 15. The jacket surface of the sleeve 23 is tangent to the recess 18.

Figures 5, 5A, 7:
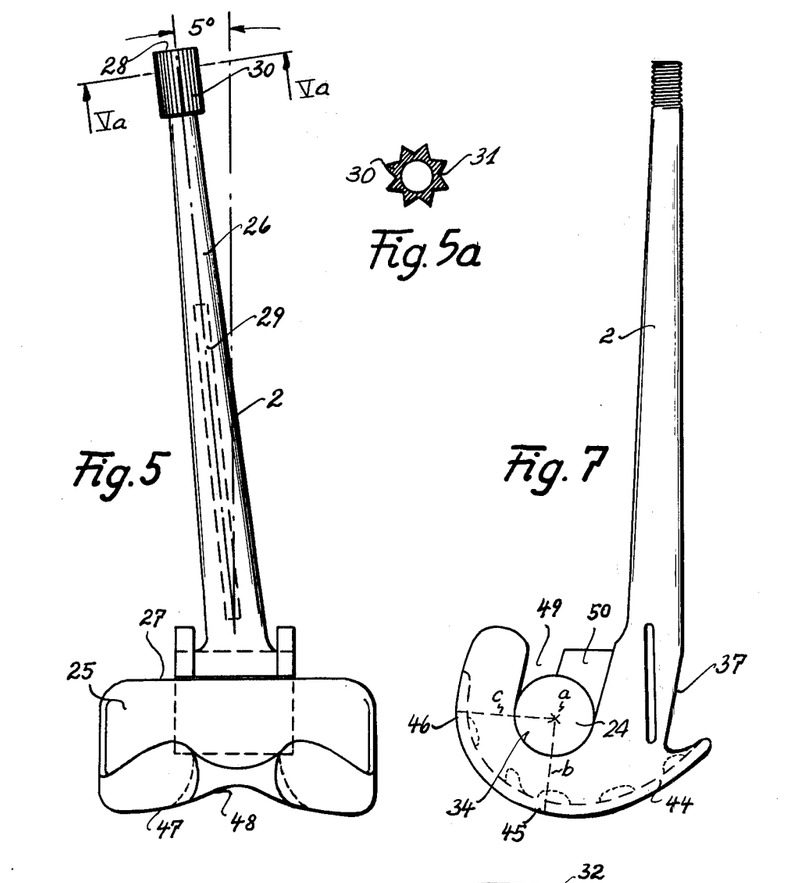
FIG. 5 is a front elevational view of a preferred embodiment of the femoral component forming part of the endoprosthesis according to the invention.
FIG. 5a is a sectional view taken along line Va—Va of FIG. 5.
FIG. 7 is a side elevational view of the femoral component.
Figure 6:
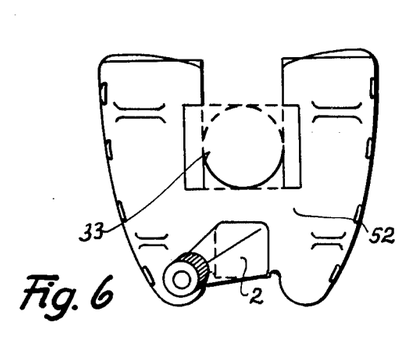
FIG. 6 is a top plan view of the femoral component.
Figure 8:
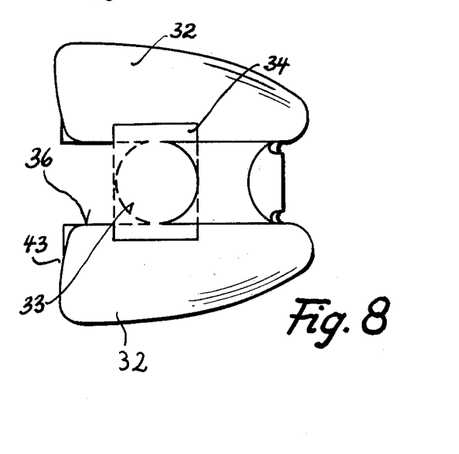
FIG. 8 is a bottom plan view of the femoral component.

A roll body 24 which is firmly connected and oriented perpendicularly to the sleeve 23 extends along that end of sleeve 23 which faces away from the insert 17. The longitudinal axis of the roll body 24 is essentially perpendicular to the plane of flexion. The longitudinal axis of the roll body 24 coincides with the pivotal axis a, as illustrated in FIGS. 4, 7 and 10 and as will be shown later. The distance of the roll body 24 from the insert 17 is dimensioned so that the bearing faces 32 (FIG. 10) of the femoral component 2 can slide over the planar surfaces 15 and thus stress the planar surfaces 15 in such a manner that compression stresses can be transmitted from the bearing faces 32 to the planar surfaces 15.

The sleeve 23 and the roll body 24 form a unit which is vertically displaceably supported on a guide stem 38 (FIG. 4). The guide stem 38 is advisably designed as a cylinder which is firmly connected with the abutment 4 and on whose surface the unit comprising the sleeve 23 and the roll body 24 is mounted to slide with an internal face 39. This type of bearing permits displacements of the Cardan bearing 16 in the vertical direction and rotational movements about the guide stem 38.

The guide stem 38 is subdivided into an upper part 40 which has a cylindrical shape and extends into the roll body 24 and an adjoining lower part 41 which extends in the direction toward the abutment 4 and which has walls in the form of a cone frustrum. In this way it is achieved that the guide stem 38 opens into the abutment 4 on as large an area as possible. Moreover, compression forces can be transmitted within limits in the region of the conical faces of the lower part 41 from the perpendicular cylinder 23 to the guide stem 38 if, as a result of friction losses at the bearing faces 32, compression stresses from the femoral component 2 are transmitted to the roll body 24. These residual compression stresses must by no means be introduced into the guide stem 38 at the upper end thereof or directly into the abutment 4 at the lower edge 42 of the sleeve 23 facing the abutment 4 since at these points there would occur relatively high areal pressures due to the small areas involved. In order to prevent in any case such areal pressures which would result in great wear, the appropriately designed internal face 39 is supported on the conical surface of the guide stem 38 so that there can be no contact between the opposing faces either at the upper end protruding into the roll body 24 or at the lower edge 42 of the sleeve 23.

It is expedient to mount the guide stem 38 elastically on the abutment 4 so that it is capable of yielding to forces acting in the direction of pressure on the roll body 24 or on the sleeve 23. In this way it is assured that all of the compression stresses are introduced into the tibial component 1 through the planar surfaces 15.

The elastic bearing for the guide stem 38 may be brought through the abutment 4 in the direction toward its lower face and be there mounted in an elastic guide 53 which may be fastened to the underside of abutment 4, as shown in FIG. 9.

Turning now to FIGS. 5, 6, 7 and 8, the femoral component 2, similar to the tibial component 1, essentially includes a bearing half 25 and a stem 26 which serves to fasten the femoral component 2 to the bone. The stem 26 is fastened in such a manner to its bottom side 27 facing away from the tibial component 1 that it exhibits a deviation of about 5° with respect to the vertical. This corresponds approximately to the physiological valgus bend in the knee joint and is taken into account by the provision of an inclination in the end 28 of the stem in the direction toward the femur which is angled inwardly with respect to the pelvis. The stem 26 terminates at the femoral bearing half 25 along a center line between the two bearing faces 32 extending essentially in the direction of flexion of the knee joint. The terminal point of the stem 26 lies in the front portion of the femoral bearing half 25 directly in front of the fulcrum of the knee joint formed by the roll body 24.

The stem 26 is conically tapered from the femoral bearing half 25 in the direction toward its end 28. It may be reinforced by ribs 29. Similarly to stem 3 of the tibial bearing half, the end 28 of stem 26 is provided with a cap 30 which is screwed onto the end 28 and which is received in the bone. As shown in FIG. 5a, the surface of the cap is provided with grooves 31 through which bone cement can be pressed in the direction toward the femoral bearing half 25 when the stem 26 is introduced into the bone cavity.

The femoral bearing half 25 essentially includes the two laterally bounding bearing faces 32 which have a skid shape. Between the two bearing faces 32 a center part 52 is provided which together with the corresponding center part of the tibial bearing half forms the Cardan bearing 16. For this purpose, it is provided with a bore 33, which in the extended state of the knee is essentially vertical and which is provided to accommodate the sleeve 23. Perpendicular to this bore 33, a cylindrical bearing socket 34 is provided whose axis is perpendicular to the plane of flexion. This cylindrical bearing socket 34 serves to accommodate the roll body 24.

Turning in particular to FIG. 7, in their region which presses the planar surfaces 15 when the knee is in an extended position, the skid-shaped bearing faces 32 have a portion 44 of a relatively larger radius of curvature. They are shaped in simulation of the anatomic shape of the condyles which forms the femoral abutment face of the natural knee joint. This part of the bearing face 32, following the shape of the condyles, changes steadily, in the direction toward the rear portion 43 of the knee joint forming the popliteal space, into a part 45 with increasing curvature which has a smaller radius of curvature than the front portion of the bearing faces 32.

This second part 45 is followed by a third part 46 which forms the rear portion 43 of the femoral bearing half 25. This third part 46 again has a large radius of curvature. It is seen that the axis a is at a smaller distance b from the part 45 than the distance c between the axis a and the part 46. This has the result that the two bearing halves 8, 25 are pressed away from one another when the knee joint is bent extensively. This distraction of the knee joint causes the extensor muscles surrounding the knee joint to be pretensioned so that, due to this pretensioning, the knee joint resiliently moves into its greatest flexion in an attenuated manner. The distraction of the knee joint is made possible by the displaceability of the Cardan bearing 16 on the guide stem 38 and the unconnected design of the pressure bearing. By displacing the Cardan bearing 16, the distance between the fulcrum of the knee joint and the tibial bearing half 8 of the pressure bearing is increased, since the unit formed of the sleeve 23 and the roll body 24 can slide on the guide stem 38 away from the tibial component 1. This results in a larger space in the popliteal area for accommodating the soft tissue surrounding the knee joint. Moreover, the extensor apparatus which has been pretensioned by the distraction of the knee joint prevents a hard abutment of the rear portions of the femoral and tibial components 2, 1, respectively, which contact one another upon substantial flexion. In this way, breakage of these parts is prevented.

The third part 46 of each bearing face 32 no longer has the skid-like design of the pressure faces. It merely has the shape of the femoral component which extends into the condyle of the femur.

In a top view, the bearing faces 32 are bounded by a line formed of circular sectors which correspond approximately to the delineation of the planar surfaces 15. As a result of this design, the planar surfaces 15 are stressed essentially uniformly by the bearing faces 32 so that the areal pressure is relatively small despite the large forces being transmitted. This design of the bearing faces 32 has the additional advantage that the bearing faces 32 are much narrower within the circular sector-shaped delineation at the points of less stress.

This makes it possible that only a small amount of bone need be removed in the area of the condyles when the femoral component 2 is implanted. Such savings in resection improve the feasibility of exchanging the implanted endoprosthesis for another one at a later time if parts of the prosthesis have come loose from the bone or other difficulties have arisen during use of the prosthesis.

Moreover, the bearing faces 32 are also curved transversely to their direction of flexing movement. This curvature 47 which has the shape of a circular sector, has a constant radius of curvature 48 so designed that the bearing faces are inclined toward one another in a tent-like manner. The inclination of the bearing faces 32 essentially corresponds to the shape of the side faces 22 which rise from the planar surfaces 15 of the tibial component 1 in the direction toward the abutment face 19. When the knee joint is in its extended position, the curved portion 47 stresses the side faces 22 so that the femoral component 2 is stabilized in the plane of flexion of the knee joint on the tibial component 1 essentially under the influence of body weight and the tension of the jacket of soft tissue surrounding the knee joint. In this position, the femoral component 2 is not rotated with respect to the tibial component 1.

The radius of curvature 48 changes along the bearing face 32 in such a manner that it is smallest in the region which is stressed when the knee is in its extended position and increases constantly in the direction toward the rear portion 43.

In this way, the play between the side faces 22 on the one hand and the tent-roof like curved portion 47 on the other hand likewise increases with increasing flexion of the knee joint, since the guidance of the curved portion 47 takes place independently from the respective degree of flexion of the knee joint always at approximately the same location on the side face 22. With this play of the bearing face 32 with respect to the planar surfaces 15, the femoral component 2 is displaced into a position where it can perform rotational movements within limits with respect to the tibial component 1, while the femoral component is guided on the Cardan bearing 16 which moves on the guide stem 38. The rotation of the femoral component 2 in the respective flexed position of the knee joint is braked only by virtue of the curved portion 47 running up on the adjacent side face 22. This generates a distraction of the knee joint against the resistance of the extensor muscles, so that the torque which effects the rotation of the femoral component 2 with respect to the tibial component 1 is then transmitted to the anchors of the components 1, 2.

A slit 36 whose width corresponds to the outer diameter of the sleeve 23 passes through the center portion 52 of the femoral component 2. This slit 36 opens into the bore 33 so that the latter is given the shape of a hollow half cylinder only in its front portion which faces away from the slit 36. The sleeve 23 is guided through slit 36 when the two components 1, 2 and assembled into a prosthesis. As soon as the roll body 24 has been hung into the cylindrical bearing socket 34, the sleeve 23 rests in the hollow half cylinder formed by the bore 33 with its frontal face oriented in the direction toward the knee cap as long as the knee joint is in the extended position. When components 1, 2 are pivoted toward each other with respect to the roll body 24, the sleeve 23 slides through slit 36 with its side parts which are disposed transversely to the plane of flexion. On the other hand, the hollow half cylinder formed by the bore 33 serves as an abutment which fixes the degree of extension of the knee joint.

Advisably the path of the bore 33 in the center portion 52 of the femoral component 2 is so designed that it is possible to overflex the knee joint by 5°.

The roll body 24 is hung into the cylindrical bearing socket 34 through a hooking opening 49. This hooking opening 49 is provided directly above the cylindrical bearing socket 34 and is oriented toward stem 26. It enables the two components 1, 2 to be assembled after they have already been anchored in their respective bones via their stems 3, 26. For effecting such an assembly, the roll body 24 is pushed over the highest portion in the rear part 43 of the bearing faces 32 so that it engages in the cylindrical bearing socket 34 under the bias produced by the extensor muscles. For this reason, it is not necessary to introduce a pivot shaft after assembly of the two components 1, 2 as required for hinge joints. In the prior art hinge joints a resection of the femor has been required so as to provide a bore for introducing the pivot shaft. Such resection, which weakens the bone, and which also increases the costs of the operation due to the additional time required, can be eliminated for the prosthesis of the present invention.

The part of the hooking opening 49 facing the stem 26 is closed by a lid 50 in order to protect the bearing formed by the roll body 24 as much as possible against contamination resulting, for example, from residuals of bone cement. The part of the hooking opening 49 adjacent the bearing faces 32 remains open to permit lubricating fluids produced by the body to enter into the cylindrical bearing socket 34.

The Cardan bearing 16 formed by the roll body 24 and the cylinder 23 is mounted in a bearing site 51 on the tibial component 1 (FIG. 4). This bearing site is advisably provided in insert 17, which, in order to form the planar surface 15, rests on the abutment 4.

A collar 54 which is permanently connected with abutment 4 and which surrounds the bearing site 51 is provided between the insert 17 and the walls of the sleeve 23. If the femoral component 2 is rotated with respect to the tibial component 1, this collar 54 prevents the walls of the sleeve 23 from exerting frictional stresses on the insert 17.

The tibial component 1 as well as the femoral component 2 are made of metal. An alloy of chromium, cobalt and molybdenum is particularly appropriate. The bearing halves 8, 25 are made of an interposed plastic. For this purpose, high molecular weight polyethylene will be useful which is already known from similar applications. Due to the high pressures to be expected, it may be necessary, under certain circumstances, to insert carbon fibers or carbon mats in the polyethylene. At points of mutual stresses, at least one part of the faces involved is made of metal, the other of plastic. Thus, the bearing faces 32 which are made of metal slide on the plastic insert 17 and the plastic sleeve 23 is guided by the metal collar 54.

The endoprosthesis according to the invention is a substantial approximation to the natural shape of the knee joint. The planar surfaces 15 are adapted to the average shape of the cross section of the head of the tibia. The ribs 10 provided at the underside serve to stabilize the plateau portion and additionally to absorb rotary forces. Finally, a massive stabilization member which also serves to support the abutment 4 may be provided at the underside of the plateau.

The arrangement of the Cardan bearing 16 in the rear portion has the advantage that when the knee joint is flexed, the soft tissue in the popliteal space cannot be compressed in a movement hindering manner. In order to permit as great a bend of the knee joint as possible, the abutment 4 is provided with the recess 18 in the region where the Cardan bearing 16 is disposed.

The horseshoe shaped planar surfaces 15 which extend beyond the recess 18 are unconnected in the region of the popliteal space in order not to produce additional obstructions there. The arrangement of the Cardan bearing 16 at the rearmost edge of the abutment 4 in the immediate vicinity of the recess 18 serves exclusively to maintain great flexibility of the knee joint.

If a sudden torque is introduced into the tibial component 1 or the femoral component 2, the design of the knee joint prosthesis according to the present invention permits, in the alternative the following sequences of movement:

(a) If the flexion of the knee joint remains constant, the curved portion 47 stresses the side face 22 of the abutment face 19 at the location corresponding to this flexion. The resulting distraction of the knee joint leads to an increase in the bearing energy of the body weight and of the internal tension in the soft tissue jacket. As soon as the external forces which have produced this torque cease the distraction of the knee joint is reversed by an equalization of the potential energy on the one hand and of the internal tension in the soft tissue jacket on the other hand so that a reverse rotation is effected.

(b) If instead, upon the introduction of a certain torque, the flexion of the knee joint does not remain constant, a distraction of the knee joint is possibly prevented or at least reduced under the influence of the body weight and the internal tension of the soft tissue jacket in that the femoral component 2 continues to slide into the flexed position on the increasing radius of curvature 48 of the curved portion 47 without the curved portion 47 being able to slide up the adjacent side face 22 of the abutment face 19. With constant deflection of the tibial component 1 with respect to the femoral component 2 by way of rotation, the knee joint prosthesis according to the invention is thus forced into a flexed position without any substantial distraction of the knee joint.

The usual function of the knee joint prosthesis will be a combination of different proportions of these two sequences of movement.

An increase in the possibility of rotation with increasing flexion can be augmented by making the curved portion 47 oblique. This obliqueness may become greater in the direction toward the rear portion 43 of the femoral component 2. This results in a relatively large play between the curved portion 47 and the side faces 22 of the abutment face 19. This play becomes evident as loose lateral excursions of the joint which, however, are kept within limits by the influence of the body weight and the pretensioned soft tissue jacket. On the other hand, such play permits movement of the joint members with respect to one another which corresponds to the physiological abduction and adduction movements.

Although the stems 3, 26 are given narrow dimensions, for reasons of keeping the required bone resection to a minimum, the stems have a high stability due to the cast-on ribs. The caps 12, 30 set on the ends of the stems 3, 26 have different sizes to correspond to the different sizes of the bone lumina.

If required, the tibial bearing halves may be made of different heights. In this way, the thickness of the bearing half can be adapted to the respective requirements during the operation, particularly to the extent of bone resection required which becomes evident only during the operation. With an appropriate selection of the thickness of the bearing halves, the tension in the joint capsule required in an individual case can be equalized or maintained.

Since the two components are not connected together by means of a shaft or in some other way, bearing parts can be exchanged without having to remove the endoprosthesis. In this way the Cardan guide member as well as the force transmitting bearing face member can be exchanged. For this purpose, it is necessary to remove bone cement from the dorsal portion of the anchor in order to reach the blocking mechanism.

It is to be understood that the above description of the present invention is susceptible to various modifications, changes and adaptations, and the same are intended to be comprehended within the meaning and range of equivalents of the appended claims.

What is claimed:

1. In a knee joint endoprosthesis including a femoral component, a tibial component and slide bearing means joining the femoral and tibial components to one another and supporting the femoral component on the tibial component; the improvement wherein said slide bearing means comprises
    (a) a platform affixed to said tibial component and having
        (1) first and second planar support surfaces spaced from one another and
        (2) an elevation situated between said planar support surfaces and rising above their level; said elevation having first and second inclined lateral surfaces oriented towards the respective first and second planar support surfaces and sloping towards the femoral component;
    (b) articulating means mounted on said platform between said planar support surfaces and adjacent said elevation; said articulating means being jointed to said femoral component to provide for flexing motions, rotary motions and shifting motions of said femoral component and said tibial component with respect to one another; said flexing motions having a pivotal axis and a direction which lies in a plane perpendicular to said planar support surfaces of said platform; said rotary motions having a rotary axis perpendicular to said planar support surfaces of said platform; said shifting motions being displacements of said femoral component and said tibial component toward or away from one another; and
    (c) first and second parallel-arranged, spaced skid-shaped members affixed to said femoral component and having respective curved first and second bearing faces normally engaging respective said first and second planar support faces of said platform; said skid-shaped members flanking said elevation, whereby upon rotary motion of said femoral and tibial components with respect to one another about said rotary axis, said first and second bearing faces run up on respective said first and second inclined lateral surfaces of said elevation effecting a shifting motion of said femoral and tibial components away from one another.

2. A knee joint endoprosthesis as defined in claim 1, wherein said elevation rises gradually from a rear of the knee joint towards a ridge of said elevation and drops steeply from said ridge towards a front of the knee joint.

3. A knee joint endoprosthesis as defined in claims 1, wherein said articulating means comprises
    (a) a guide stem mounted on said platform and extending towards said femoral component in an orientation perpendicular to said planar support surfaces;
    (b) a sleeve member having an axial cylindrical opening therein and being rotatably and axially slidably inserted on said guide stem in a substantially coaxial relationship therewith;
    (c) a cylindrical roll body rigidly affixed to an end of said sleeve member and having a longitudinal axis coinciding with said pivotal axis; and
    (d) a cylindrical bearing socket forming part of said femoral component for receiving said roll body in a conforming relationship therewith, whereby said roll body and said bearing socket pivotally couple said femoral and tibial components to one another and further whereby said sleeve member rotatably and axially slidably couples said femoral component to said guide stem.

4. A knee joint endoprosthesis as defined in claim 3, wherein said cylindrical roll body includes a radially extending bore aligned with said cylindrical opening in said sleeve member; said guide stem extending from said cylindrical opening of said sleeve member into said radially extending bore of said cylindrical roll body.

5. A knee joint endoprosthesis as defined in claim 3, wherein said cylindrical bearing socket comprises first and second socket parts formed on respective said first and second skid-shaped members; said first and second socket parts receiving respective length portions of said roll body extending in opposite directions from said sleeve member.

6. A knee joint endoprosthesis as defined in claim 3, wherein said guide stem has a cylindrical upper part remote from said platform and a frustoconical lower part widening towards said platform; the cross-sectional shape of said axial opening in said sleeve member and said bore in said roll body conforming to the respective frustoconical and cylindrical parts of said guide stem.

7. A knee joint endoprosthesis as defined in claim 6, wherein said sleeve member terminates at a clearance from said platform.

8. A knee joint endoprosthesis as defined in claim 3, further comprising a collar affixed to said platform for guiding said sleeve member.

9. A knee joint endoprosthesis as defined in claim 3, further comprising means for resiliently supporting said guide stem with respect to said platform.

10. A knee joint endoprosthesis as defined in claim 9, wherein said platform has an underside oriented away from said sleeve member and wherein said guide stem passes through said platform to said underside; further comprising an elastic guide attached to said underside; said guide stem being supported in said elastic guide.

11. A knee joint endoprosthesis as defined in claim 3, wherein the bearing socket surrounds said roll body in a hook-like manner in a direction parallel to the plane of flexion and further wherein said bearing socket has an upper opening for permitting insertion of said roll body into said bearing socket in a hooked position.

12. A knee joint endoprosthesis as defined in claim 11, further comprising a lid partially extending over said upper opening of said bearing socket.

13. A knee joint endoprosthesis as defined in claim 1, wherein said curved bearing faces have a slightly convex course in a direction transverse to the direction of said flexing motion.

14. A knee joint endoprosthesis as defined in claim 13, wherein said slightly convex course is bounded by a sector of a circular arc.

15. A knee joint endoprosthesis as defined in claim 14, wherein said slightly convex course has a varying radius of curvature along a length dimension of said curved bearing faces.

16. A knee joint endoprosthesis as defined in claim 15, wherein said circular arc extends to a mid portion of said femoral component and has a radius of curvature which increases from that zone of said curved bearing faces that are effective at small flexions to that zone of said curved bearing faces that are effective at large flexions.

17. A knee joint endoprosthesis as defined in claim 13, wherein the shape of said inclined lateral surfaces is complemental to said slightly convex course of said curved bearing faces when the knee joint is in its extended state.

18. A knee joint endoprosthesis as defined in claim 17, wherein said curved bearing faces have outer bounding lines of circular arc shape essentially corresponding to outer bounding lines of said planar surfaces.

19. A knee joint endoprosthesis as defined in claim 18, wherein said curved bearing faces are narrower in the zone with which they engage the respective planar support surfaces in the extended state of the knee joint than in the zone with which they engage the respective planar support surfaces in the strongly flexed state of the knee joint.

20. A knee joint endoprosthesis as defined in claims 1, wherein at least one of said components has a stem having a terminus; a cap attached to said terminus for centering said cap in a bone; said stem having a cylindrical outer face provided with grooves extending generally parallel to the length dimension of said stem.

21. A knee joint endoprosthesis as defined in claim 20, wherein said cap has a star-like cross-sectional configuration, and further wherein said grooves have a depth extending to the middle of the wall thickness of said cap.

22. A knee joint endoprosthesis as defined in claim 21, wherein said cap threadedly engages said terminus of said stem.

23. In a knee joint endoprosthesis including a femoral component, a tibial component and slide bearing means joining the femoral and tibial components to one another and supporting the femoral component on the tibial component; the improvement wherein said slide bearing means comprises
(a) a platform affixed to said tibial component and having first and second planar support surfaces spaced from one another;
(b) articulating means mounted on said platform between said planar support surfaces; said articulating means having a pivotal axis generally parallel to said planar support surfaces; said articulating means being jointed to said femoral component to provide for flexing motions of said femoral component and said tibial component with respect to one another about said pivotal axis; said flexing motions further having a direction which lies in a plane perpendicular to said planar support surfaces; said articulating means further providing for shifting motions of said femoral component and said tibial component toward and away from one another; said articulating means comprising
   (1) a guide stem mounted on said platform and extending towards said femoral component in an orientation perpendicular to said planar support surfaces;
   (2) a sleeve member having an axial cylindrical opening therein and being rotatably and axially slidably inserted on said guide stem in a substantially coaxial relationship therewith;
   (3) a cylindrical roll body rigidly affixed to an end of said sleeve member and having a longitudinal axis coinciding with said pivotal axis; and
   (4) a cylindrical bearing socket forming part of said femoral component for receiving said roll body in a conforming relationship therewith, whereby said roll body and said bearing socket pivotally couple said femoral and tibial components to one another and further whereby said sleeve member rotatably and axially slidably couples said femoral component to said guide stem; and
(c) first and second parallel-arranged, spaced skid-shaped members affixed to said femoral component and having respective curved first and second bearing faces progressively engaging respective said first and second planar support faces of said platform as said femoral and tibial components pivot with respect to one another from an extended position through an initial flexed position to a maximum flexed position; those portions of said arcuate first and second bearing faces which are in engagement with the respective said first and second planar support faces in said initial flexed position of said femoral and tibial components are at a smaller distance from said pivotal axis than those portions of said arcuate first and second bearing faces which are in engagement with the respective said first and second planar support faces in said maximum flexed position of said femoral and tibial components, whereby said femoral and tibial components shift away from one another when they flex from said initial flexed position into said maximum flexed position.

24. A knee joint endoprosthesis as defined in claim 23, wherein said cylindrical roll body includes a radially extending bore aligned with said cylindrical opening in said sleeve member; said guide stem extending from said cylindrical opening of said sleeve member into said radially extending bore of said cylindrical roll body.

25. A knee joint endoprosthesis as defined in claim 23, wherein said cylindrical bearing socket comprises first and second socket parts formed on respective said first and second skid-shaped members; said first and second socket parts receiving respective length portions of said roll body extending in opposite directions from said sleeve member.

26. A knee joint endoprosthesis as defined in claim 23, wherein said guide stem has a cylindrical upper part remote from said platform and a frustoconical lower part widening towards said platform; the cross-sectional shape of said axial opening in said sleeve member and said bore in said roll body conforming to the respective frustoconical and cylindrical parts of said guide stem.

27. A knee joint endoprosthesis as defined in claim 26, wherein said sleeve member terminates at a clearance from said platform.

28. A knee joint endoprosthesis as defined in claim 23, further comprising means for resiliently supporting said guide stem with respect to said platform.

29. A knee joint endoprosthesis as defined in claim 28, wherein said platform has an underside oriented away from said sleeve member and wherein said guide stem passes through said platform to said underside; further comprising an elastic guide attached to said underside; said guide stem being supported in said elastic guide.

30. A knee joint endoprosthesis as defined in claim 23, wherein the bearing socket surrounds said roll body in a hook-like manner in a direction parallel to the plane of flexion and further wherein said bearing socket has an upper opening for permitting insertion of said roll body into said bearing socket in a hooked position.

31. A knee joint endoprosthesis as defined in claim 30, further comprising a lid partially extending over said upper opening of said bearing socket.

32. A knee joint endoprosthesis as defined in claim 23, further comprising a collar affixed to said platform for guiding said sleeve member.

* * * * *